United States Patent [19]

Allcock et al.

[11] Patent Number: 5,562,909
[45] Date of Patent: Oct. 8, 1996

[54] PHOSPHAZENE POLYELECTROLYTES AS IMMUNOADJUVANTS

[75] Inventors: Harry R. Allcock, State College, Pa.; Alexander K. Andrianov, Belmont; Robert S. Langer, Newton, both of Mass.; Karyn B. Visscher, State College, Pa.

[73] Assignees: Massachusetts Institute of Technology, Cambridge, Mass.; Virus Research Institute, University Park, Pa.; The Penn State Research Foundation, Cambridge, Mass.

[21] Appl. No.: 90,841

[22] Filed: Jul. 12, 1993

[51] Int. Cl.$^6$ .................................................. A61K 39/39
[52] U.S. Cl. ............................ 424/280.1; 424/70.11; 424/193.1; 424/499; 424/497
[58] Field of Search .............................. 424/280.1, 208.1, 424/227.1, 499, 497, 193.1, 199.1, 204.1, 234.1, 93.1, 93.4, 93.6, 70.11

[56] References Cited

U.S. PATENT DOCUMENTS

| | | |
|---|---|---|
| 3,893,980 | 7/1975 | Allcock et al. . |
| 4,026,839 | 5/1977 | Dieck et al. . |
| 4,055,520 | 10/1977 | Dieck et al. . |
| 4,073,824 | 2/1978 | Dieck et al. . |
| 4,073,825 | 2/1978 | Dieck et al. . |
| 4,094,971 | 6/1978 | Chedid et al. . |
| 4,209,014 | 6/1980 | Sefton . |
| 4,353,888 | 10/1982 | Sefton . |
| 4,440,921 | 4/1984 | Allcock et al. . |
| 4,451,647 | 5/1984 | Allcock et al. . |
| 4,495,174 | 1/1985 | Allcock et al. . |
| 4,636,387 | 1/1987 | Allcock et al. . |
| 4,880,622 | 11/1989 | Allcock et al. . |
| 4,946,938 | 8/1990 | Magill et al. . |
| 4,975,280 | 12/1990 | Schacht et al. . |
| 5,053,451 | 10/1991 | Allcock et al. . |
| 5,104,947 | 4/1992 | Schacht et al. . |
| 5,109,026 | 4/1992 | Hoskinson et al. . |
| 5,126,147 | 6/1992 | Silvestri et al. ......................... 424/497 |
| 5,149,543 | 9/1994 | Cohen et al. ............................ 424/499 |

FOREIGN PATENT DOCUMENTS

| | | |
|---|---|---|
| 0168277 | 1/1986 | European Pat. Off. . |
| 0539571 | 5/1993 | European Pat. Off. . |
| 9205778 | 4/1992 | WIPO . |

OTHER PUBLICATIONS

Grolleman, C. W. J., et al., "Studies on a Bioerodible Drug Carrier System Based on Polyphosphazene." *J. Cont. Release* 3:143–154 (1986).
Petrov. et al., *Zhurnal Vsesovuznogo Khimicheskogo Obshchestva im. D. I. Mendeleeva*, 33:22–42 (1988).
Allison et al in *Vaccines: New Approaches to immunological problems* ed by R. W. Ellis, 1992, Butterworth–Heineman; pp. 431–449.
Gupta et al (1993) Vaccines 11(3): 293–306.
Goedemaed et al (1991) J. Controlled Release 170:245–258.
Grolleman et al (1986) J. Controlled Rease 4:119–131.
Allcock et al (1983) 16(4 and 9):715–719 and 1401–1406.
Crommen et al (1993) J. Controlled Rel. 24:167–180.
Allcock, H. R., "A New Approach to Polymer Chemistry: Organometallic and Bioactive Phosphazenes", *Journal of Polymer Science: Polymer Symposium*, 70:71–77 (1983).
Allcock, H. R. et al., "Activity of urea amidohydrolase immobilized within poly[di(methoxyethoxyethoxy)phosphazene] hydrogels", *Biomaterials*, 00(0) (1994).
Allcock, H. R. et al., "Alkanesulfonation of Cyclic and High Polymeric Phosphazenes", *Macromolecules*, 26:5512–5519 (1993).
Allcock, H. R., et al., "Amphiphilic polyphosphazenes as membrane materials: influence of side group on radiation crosslinking", *Biomaterials*, 9:500–508 (1988).
Allcock, H. R., et al., "An Ionically Cross–Linkable Polyphosphazene: Poly[bis(carboxylatophenoxy)phosphazene] and Its Hydrogels and Membranes", *Macromolecules*, 22:75–79 (1989).
Allcock, H. R., et al., "Antibacterial Activity and Mutagenicity Studies of Water–Soluble Phosphazene High Polymers", *Biomaterials*, 13(12):857–862 (1992).
Allcock, H. R., "Chemical Synthesis at the Boundary between Polymer Chemistry and Inorganic Materials", *The Chemist*, 10–16 (Jan. 1990).
Allcock, H. R. et al., "Coupling of Cyclic and High–Polymeric [(Aminoaryl)oxy]phosphazenes to Carboxylic Acids: Prototypes for Bioactive Polymers", *Macromolecules*, 15:693–696 (1982).
Allcock, H. R., et al., "Covalent Linkage of Proteins to Surface–Modified Poly(organophosphazenes): Immobilization of Glucose–6–Phosphate Dehydrogenase and Trypsin", *Macromolecules*, 19:1502–1508 (1986).
Allcock, H. R., "Cyclic and High–Polymeric Phosphazenes as Carrier Molecules for Carboranyl, Metallo, or Bioactive Side Groups", *ALS Symp. Ser.*, 232:49–67 (1983).
Allcock, H. R., "Developments at the Interface of Inorganic, Organic and Polymer Chemistry", *Chemical and Engineering News*, 63:22–36 (1985).
Allcock, H. R., et al., "Diazo Coupling Reactions with Poly(organophosphazenes)", *Macromolecules*, 14:1622–1625 (1981).
Allcock, H. R., et al. "Effects of Organic Side Group Structures on the Properties of Poly(organophosphzenes)", *Macromolecules*, 21:323–334 (1988).
Allcock, H. R.., et al., "Functionalization of the Surface of Poly[bis(trifluoroethoxy)phosphazene] by Reactions with Alkoxide Nucleophiles", *Materials*, 3:450–454 (1991).

(List continued on next page.)

*Primary Examiner*—Kay K. A. Kim
*Attorney, Agent, or Firm*—Arnall Golden & Gregory

[57] ABSTRACT

A immunoadjuvant soluble phosphazene polyelectrolyte is disclosed. In one embodiment, the polymeric adjuvant is an poly(organophosphazene) with (i) ionized or ionizable pendant groups that contain, for example, carboxylic acid, sulfonic acid, or hydroxyl moieties, and (ii) pendant groups that are susceptible to hydrolysis under the conditions of use, to impart biodegradability to the polymer.

6 Claims, No Drawings

OTHER PUBLICATIONS

Allcock, H. R., et al., "Glyceryl Polyphosphazenes: Synthesis, Properties and Hydrolysis", *Macromolecules*, 21:1980–1985 (1988).

Allcock, H. R., et al., "Hydrolysis Pathways for Aminophosphazenes", *Inorg. Chem.*, 21:515–521 (1982).

Allcock, H. R., et al., "Hydrophilic Polyphosphazenes as Hydrogels: Radiation Cross–linking and Hydrogel Characteristics of Poly[bis(methoxyethoxyethoxy)phosphazene]", *Biomaterials*, 9:509–513 (1988).

Allcock, H. R., "Organometallic and Bioactive Cyclophosphazenes, and the Relationship to Inorganic Macromolecules", *Phosphorus Sulfur, and Silica*, 41:119–133 (1989).

Allcock, H. R., et al., "Organosilicon Derivatives of Cyclic and High Polymeric Phosphazenes", *J. Organometallic Chemistry*, 341:231–239 (1988).

Allcock, H. R., et al., "Organosilylphosphazene Oligomers and Polymers: Synthesis via (Lithioaryloxy)phosphazenes", *Macromolecules*, 22:3571–3578 (1989).

Allcock, H. R., et al, "Organosiloxyphosphazene Polymers: Synthesis via Aminosiloxane Reagents", *Macromolecules*, 23,:1626–1635 (1990).

Allcock, H. R., et al., "Oxidation of Poly[bis(4–methylphenoxy)phosphazene] Surfaces and Chemistry of the Surface Carboxylic Acid Groups", *Materials*, 4:769–775 (1992).

Allcock, H. R., et al., "Phosphazene High Polymers with Bioactive Substituent Groups; Prospective Anesthetic Aminophosphazenes", *Macromolecules*, 15(3):689–693 (1982).

Allcock, H. R., et al. "Phosphonitrilic Compounds, XV. High Molecular Weight Poly[bis(amino)phosphazenes] and Mixed–Substitunent Poly(aminophosphazenes)", *Inorganic Chemistry*, 11(7):2584–2590 (1972).

Allcock, H. R., et al., Poly[(aryloxy)carbophosphazenes]: Synthesis, Properties, and Thermal Transition Behavior, Macromolecules, 24:2024–2028 (1991).

Allcock, H. R., "Poly(organophosphazenes) Designed For Biomedical Uses", *Organometallic Polymers*, New York: Academic Press, pp. 283–288 (1978).

Allcock, H. R., et al., "Poly(organophosphazenes) with Azoxybenzene Side Groups, Synthesis and Morphology", *Macromolecules*, 24:2841–2845 (1991).

Allcock, H. R., et al, "Poly(organophosphazenes) with Oligopeptides as Side Groups: Prospective Biomaterials", *Macromolecules*, 24:993–999 (1991).

Allcock, H. R., et al., "Poly(organophosphazenes) with Poly(alkyl ether) Side Groups: A Study of Their Water Solubility and the Swelling Characteristics of Their Hydrogels", *Macromolecules*, 25:5573–5577 (1992).

Allcock, H. R., "Polyphosphazenes", *J. of Inorganic and Organometallic Polymers*, 2(2):197–211 (1992).

Allcock, H. R., "Polyphosphazenes as New Biomedical and Bioactive Materials", *In Biodegradable Polymers as Drug Delivery Systems*, eds. R. Langer and M. Chasin, Marcel Dekker: New York, pp. 163–193 (1990).

Allcock, H. R., et al., "Polyphosphazene–Organic Polymer Interpenetrating Polymer Networks", *Materials*, 4:1188–1192 (1992).

Allcock, H. R., et al., "Polyphosphazenes with Etheric Side Groups: Prospective Biomedical and Solid Electrolyte Polymers", *Macromolecules*, 19:1508–1512 (1986).

Allcock, H. R., et al., "Polyphosphazenes with Glucosyl and Methylamino, Trifluoroethoxy, Phenoxy, or (Methoxyethoxy)ethoxy Side Groups", *Macromolecules*, 24:23–34 (1991).

Allcock, H. R., et al. "Preparation and Characterization of Poly(organophosphazene) Blends", *Material*, 4:1182–1187 (1992).

Allcock, H. R., "Rational Design and Synthesis of New Polymeric Materials", *Science*, 255:1106–1112 (1992).

Allcock, H. R., et al., "Ring–Opening Polymerization of Methylsilane– and Methylsiloxane–Substituted Cyclotriphosphazenes", *Macromolecules*, 21:1–10 (1988).

Allcock, H. R., et al., "Schiff Base Coupling of Cyclic and High–Polymeric Phosphazenes to Aldehydes and Amines: Chemotherapeutic Models", *Macromolecules*, 14:1615–1622 (1981).

Allcock, H. R., et al., "Surface Reaction of Poly[bis(trifluoroethoxy)phosphazene] Films by Basic Hydrolysis", *Materials*, 3:442–449 (1991).

Allcock, H. R., et al., "Synthesis and Properties of High Polymeric Phosphazenes with (Trimethylsilyl)methyl Side Groups", *Macromolecules*, 26:764–771 (1993).

Allcock, H. R., et al., "Synthesis and Reactivity of Cyclotriphosphazenes Bearing Reactive Silane Functionalities: Novel Derivatives via Hydrosilylation Reactions", *Organometallics*, 10:3819–3825 (1991).

Allcock, H. R., et al., "Synthesis of High Polymeric Alkoxy– and Aryloxyphosphonitriles", *Journal of the American Chemical Society*, 87(18):4216–4217 (1965).

Allcock, H. R., et al., "Synthesis of New Polyphosphazene Elastomers", *Macromolecules*, 23:3873–3877 (1990).

Allcock, H. R., et al., "Synthesis of Poly[(amino acid alkyl ester)phosphazenes]", *Macromolecules*, 10(4):824–830 (1977).

Allcock, H. R.., et al., "Synthesis of Poly[bis(phosphazo)phosphazenes] Bearing Aryloxy and Alkoxy Side Groups", *Macromolecules*, 25:2802–2810 (1992).

Allcock, H. R., et al., "Synthesis of Polyphosphazenes Bearing Geminal (Trimethylsilyl)methylene and Alkyl or Phenyl Side Groups", *Macromolecules*, 22:1534–1539 (1989).

Allcock, H. R., et al., "Synthesis of Polyphosphazenes with Isothiocyanato, Thiourethane, and Thiourea Side Groups", *Macromolecules*, 24:2852–2857 (1991).

Allcock, H. R., "Tailored Design of New Polyphosphazenes with Special Properties", *Progress in Pacific Polymer Science*, ed. Y. Imanishi. Springer–Verlag Berlin Heidelberg, pp 89–100 (1992).

Allcock, H. R., "The Current State of the Art in the Synthesis of Inorganic Organometallic Polymers", *Inorganic and Organometallic Polymers with Special Properties*, ed. Laine, Kluwer Academic Publishers, pp. 43–62. (1992).

Allcock, H. R., et al., "Thin–Layer Grafts of Poly[bis-((methoxyethoxy) ethoxy)phosphazene] on Organic Polymer Surfaces," 4:775–780 (1992).

Coltrain, B. K., et al., "Polyphosphazene Molecular Composites, 1. In Situ Polymerization of Tetraethoxysilane", *Chem. Mater.*, 4:358–364 (1992).

Eldridge, J. H., et al., "Biodegradable Micropheres: Vaccine Delivery System for Oral Immunization", *Microbiology and Immunology*, 146:59–66 (1989). Grolleman, et al., *J. Controlled Release*, 3:143 (1986)*.

Landry, Christine, et al., "Novel Miscible Blends of Etheric Polyphosphazenes with Acidic Polymers", *Macromolecules*, 26:35–46 (1993).

Laurencin, C. T., et al., "Controlled release using a new bioerodible polyphosphazene matrix system", *Journal of Biomedical Materials Research*, 21:1231–1246 (1987).

Laurencin, C. T., et al., "Use of Polyphosphazenes for Skeletal Tissue Regeneration", *J. Biomed. Mater. Res.*, 27:963–973 (1993).

Mark, J. E., et al., "Polyphosphazenes", *Inorganic Polymers*, ed. Prentice–Hall, pp. 61–139 (1992).

Neenan, T. X., et al., "Synthesis of a heparinized poly(organophosphazene)", *Biomaterials*, 3:78–80 (1982).

Ngo, D. C., et al., "Poly(phosphazophosphazenes): A New Class of Inorganic Polymers with Short–Chain Branching", *Journal of the American Chemical Society*, pp. 113–114 (1991).

Novak, M., et al., "Murine model for evaluation of protective immunity to influenza virus", *Vaccine*, 11(1):55–60 (1993).

Payne, L. G., et al., "Xenobiotic Polymers as Vaccine Vehicles", *7th International Congress of Mucosal Immunology*, Prague, Czechoslovakia, Aug. 16–20, 1992.

Petrov, et al., *Jhurnal Vses, Khim. Ob–va im. D. I. Mendeleeva*, 33:22–42 (1988)*.

Petrov, et al., *Sov. Med. Rev. D. Immunol.*, 4:1–113 (1992)*.

Shapiro, A., et al., "Efficacies of Vaccines containing Alginate Adjuvant", *J. appl. Bact.*, 30(2):304–311 (1967).

Shechmeister, I. L., et al., "Use of Sodium Alginate Adjuvant in Immunization Against Equine Influenza", *Am. J. Vet. Res.*, 28(126):1373–1378 (1967).

Visscher, K. B., et al., "Synthesis and Characterization of Polyphosphazene Interpenetrating Polymer Networks", *Polymeric Materials Science & Engineering*, 65:3–4 (1991).

Visscher, K. B., et al., "Synthesis and Properties of Polyphosphazene Interpenetrating Polymer Networks", *Macromolecules*, 23(22):4885–4886 (1990).

PHOSPHAZENE POLYELECTROLYTES AS IMMUNOADJUVANTS

BACKGROUND OF THE INVENTION

This application is in the area of polymers for biomedical applications, and in particular describes polymers that can be used as immunoadjuvants.

Vaccine Development

A wide variety of antigens stimulate the production of antibodies in animals and confer protection against subsequent infection. However, some antigens are unable to stimulate an effective immune response.

The immunogenicity of a relatively weak antigen is often enhanced by the simultaneous administration of the antigen with an adjuvant, a substance that is not immunogenic when administered alone, but will induce a state of mucosal and/or systemic immunity when combined with the antigen. It has been traditionally thought that adjuvants, such as mineral oil emulsions or aluminum hydroxide, form an antigen depot at the site of injection that slowly releases antigen. Recent studies by Allison and Byars, in: "Vaccines: New Approaches to Immunological Problems":, R. W. Ellis, ed., p. 431, Butterworth-Heinemann, Oxford (1992) indicate that adjuvants enhance the immune response by stimulating specific and sometimes very narrow branches of the immune response by the release of cytokines. Unfortunately, many immunoadjuvants, such as Freund's Complete Adjuvant, are toxic and are therefore only useful for animal research purposes, not human vaccinations. Freund's Complete Adjuvant contains a suspension of heat-killed *Mycobacterium tuberculosis* in mineral oil containing a surfactant and causes granulomatous lesions in animals at the site of immunization. Freund's adjuvant may also cause the recipient of a vaccine to test positive for tuberculosis. Some synthetic polyelectrolytes have been found to provide immunostimulation when combined with an antigen. For example, the adjuvant activity of polyacrylic acid (PAA), copolymers of acrylic acid and N-vinylpyrrolidone (CP-AA-VPD), poly-2-methyl-5-vinyl pyridine (PMVP), poly-4-vinyl-N-ethylpyridinium bromide (PVP-$R_2$) and similar compounds, when conjugated to an antigen, has been studied by Petrov et. al., *Jhurnal Vses. Khim. Ob-va im. D. I. Mendeleeva*, 33:22–42 (1988). The immunomodulatory effect of polyelectrolyte complexes containing many of these same polyelectrolytes has also been more recently reviewed by Petrov, et al., *Sov. Med. Rev. D. Immunol.*, 4:1–113 (1992). However, the toxicity and biodegradability of these polymers has not been studied and may prevent use of these polymers as adjuvants for use in humans.

A non-toxic adjuvant or carrier having the ability to stimulate an immune response to non-antigenic or weakly antigenic molecules would be useful in the development and administration of vaccines.

Therefore, it is an object of the present invention to provide an adjuvant that can be safely administered to humans and animals with minimal toxicity.

It is a further object of the present invention to provide an adjuvant that is soluble and biodegradable.

It is a further object of the present invention to provide a vaccine that confers protection against an organism such as the influenza virus or *Clostridium tetani* bacteria.

It is a further object of the present invention to provide a rapid and efficient method of synthesizing a polymer, such as polyphosphazene, for use as an adjuvant.

SUMMARY OF THE INVENTION

A synthetic, water-soluble polyphosphazene is disclosed for use as an adjuvant. In a preferred embodiment, the phosphazene is a polyelectrolyte that is biodegradable and that exhibits minimal toxicity when administered to animals, such as humans.

In one embodiment, the polymeric adjuvant is an poly(organophosphazene) with (i) ionized or ionizable pendant groups that contain, for example, carboxylic acid, sulfonic acid, or hydroxyl moieties, and (ii) pendant groups that are susceptible to hydrolysis under the conditions of use, to impart biodegradability to the polymer. Suitable hydrolyzable groups include, for example, chlorine, amino acid, amino acid ester, imidazole, glycerol, and glucosyl.

Two examples of polyphosphazenes that are useful as immunoadjuvants are poly[di(carboxylatophenoxy)phosphazene-co-di(glycinato)phosphazene-co-(carboxylatophenoxy)(glycinato)phosphazene] and poly[di(carboxylatophenoxy)phosphazene-co-di(chloro)phosphazene-co-(carboxylatophenoxy)(chloro)phosphazene].

A vaccine composition is prepared by either mixing or conjugating the polymer adjuvant with an antigen prior to administration. Alternatively, the polymer and antigen can be administered separately to the same site.

When cross-linked with a multivalent ion, the polymer becomes less soluble, resulting in slower release of the polymer from the site of administration.

DETAILED DESCRIPTION OF THE INVENTION

The term amino acid, as used herein, refers to both natural and synthetic amino acids, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(lower alkyl), —$CO_2H$, —$SO_3H$, —$PO_3H$, —$CO_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "pharmaceutically acceptable cation" refers to an organic or inorganic moiety that carries a positive charge and that can be administered as a countercation in a phosphazene polyelectrolyte.

The term heteroalkyl, as used herein, refers to a alkyl group that includes a heteroatom such as oxygen, sulfur, or nitrogen (with valence completed by hydrogen or oxygen) in the carbon chain or terminating the carbon chain.

A synthetic polymer is provided for use as an immunoadjuvant. The polymer adjuvant is a polyphosphazene that is at least partially soluble in water (typically to an extent of at least 0.001% by weight), an aqueous buffered salt solution, or aqueous alcohol solution. The polyphosphazene preferably contains charged side groups, either in the form of an acid or base that is in equilibrium with its counter ion, or in the form of an ionic salt thereof.

The polymer is preferably biodegradable and exhibits minimal toxicity when administered to animals, including humans.

Selection of Polyphosphazene Polyelectrolytes.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

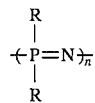

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino- including alkylamino-, heteroaralkyl, di(aliphatic)amino- including dialkylamino-, arylamino-, diarylamino-, alkylarylamino-, -oxyaryl including but not limited to -oxyphenyl$CO_2H$, -oxyphenyl$SO_3H$, -oxyphenylhydroxyl and -oxyphenyl$PO_3H$; -oxyaliphatic including -oxyalkyl, -oxy(aliphatic)$CO_2H$, -oxy(aliphatic)$SO_3H$, -oxy(aliphatic)$PO_3H$, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, -thioaralkyl, —NHC(O)O-(aryl or aliphatic), —O—[$(CH_2)_xO$]$_y$—$CH_2)_xNH_2$, —O—[$(CH_2)_xNH(CH_2)_xSO_3H$, and —O—[$(CH_2)_xO$]$_y$-(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

In one embodiment, the immunoadjuvant is a biodegradable polyphosphazene of the formula:

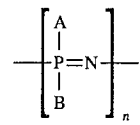

wherein A and B can vary independently in the polymer, and can be:

(i) a group that is susceptible to hydrolysis under the conditions of use, including but not limited to chlorine, amino acid, amino acid ester (bound through the amino group), imidazole, glycerol, or glucosyl; or (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic)amino- including dialkylamino-, arylamino-, diarylamino-, alkylarylamino-, -oxyaryl including but not limited to -oxyphenyl$CO_2H$, -oxyphenyl$SO_3H$, -oxyphenylhydroxyl and -oxyphenyl$PO_3H$; -oxyaliphatic including -oxyalkyl, -oxy(aliphatic)$CO_2H$, -oxy(aliphatic)$SO_3H$, -oxy(aliphatic)$PO_3H$, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, or thioaralkyl;

wherein the polymer contains at least one percent or more, preferably 10 percent or more, and more preferably 80 to 90 percent or more, but less than 100%, of repeating units that are not susceptible to hydrolysis under the conditions of use, and wherein n is an integer of 4 or more, and preferably between 10 and 20,000.

It should be understood that certain groups, such as heteroaromatic groups other than imidazole, hydrolyze at an extremely slow rate under neutral aqueous conditions, such as that found in the blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer.

In other embodiments, the immunoadjuvant is: (i) a nonbiodegradable polyphosphazene wherein none, or virtually none, of the pendant groups in the polymer are susceptible to hydrolysis under the conditions of use, or (ii) a completely biodegradable polyphosphazene wherein all of the groups are susceptible to hydrolysis under the conditions of use (for example, poly[di(glycinato)phosphazene]).

Phosphazene polyelectrolytes are defined herein as polyphosphazenes that contain ionized or ionizable pendant groups that render the polyphosphazene anionic, cationic or amphophilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte immunoadjuvant contains pendant groups that include carboxylic acid, sulfonic acid, or hydroxyl moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

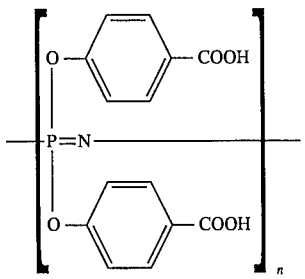

wherein n is an integer, preferably an integer between 10 and 10,000. This polymer has the chemical name poly[di(carboxylatophenoxy)phosphazene]or, alternatively, poly[bis-(carboxylatophenoxy)phosphazene](PCPP).

The phosphazene polyelectrolyte is preferably biodegradable to prevent eventual deposition and accumulation of polymer molecules at distant sites in the body, such as the spleen. The term biodegradable, as used herein, means a polymer that degrades within a period that is acceptable in the desired application, typically less than about five years and most preferably less than about one year, once exposed to a physiological solution of pH 6–8 at a temperature of approximately 25° C. –37° C.

Most preferably the polymer is a poly(organophosphazene) that includes pendant groups that include carboxylic acid moieties that do not hydrolyze under the conditions of use and pendant groups that are susceptible to hydrolysis under the conditions of use. Examples of preferred phosphazene polyelectrolytes with hydrolysis-sensitive groups are poly[di(carboxylatophenoxy)phosphazene-co-di(amino acid)phosphazene-co(carboxylatophenoxy)(amino acid) phosphazene], specifically including poly[di(carboxylatophenoxy)phosphazene-co-di(glycinato)phosphazene-co-(carboxylatophenoxy)(glycinato)phosphazene], and poly [di(carboxylatophenoxy)phosphazene-co-di(chloro)phosphazene-co(carboxylatophenoxy)(chloro)phosphazene].

The toxicity of the polyphosphazene can be determined using cell culture experiments well known to those skilled in the art. For example, toxicity of poly[di(carboxylatophenoxy)phosphazene] was determined in cell culture by coating cell culture dishes with the poly[di(carboxylatophenoxy) phosphazene]. Chicken embryo fibroblasts were then seeded onto the coated petri dishes. Three days after seeding the chicken embryo fibroblasts, the cells had become flattened and spindles formed. Under phase contrast microscopy, mitotic figures were observed. These observations provide evidence of the non-toxicity of poly[di(carboxylatophenoxy)phosphazene] to replicating cells.

Crosslinked polyphosphazenes for use as immunoadjuvants can be prepared by combining a phosphazene polyelectrolyte with a metal multivalent cation such as zinc, calcium, bismuth, barium, magnesium, aluminum, copper, cobalt, nickel, or cadmium.

Synthesis of Phosphazene Polyelectrolytes

Polyphosphazenes, including phosphazene polyelectrolytes, can be prepared by a macromolecular nucleophilic substitution reaction of poly(dichlorophosphazene) with a wide range of chemical reagents or mixture of reagents in accordance with methods known to those skilled in the art. Preferably, the phosphazene polyelectrolytes are made by reacting the poly(dichlorophosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly-(dichlorophosphazene) and the reaction conditions as necessary. Preferred polyphosphazenes for immunoadjuvant activity have a molecular weight of over 1,000.

For example, poly[(carboxylatophenoxy)(glycinato) phosphazene] (PC-G1PP) is prepared by the nucleophilic substitution reaction of the chlorine atoms of the poly-(dichlorophosphazene) with propyl p-hydroxybenzoate and ethyl glycinato hydrochloride (PC-G1PP synthesis). The poly[(aryloxy)(glycinato)phosphazene] ester thus obtained is then hydrolyzed to the corresponding poly(carboxylic acid). Other polyphosphazenes can be prepared as described by Allcock, H. R.; et al., *Inorg. Chem.* 11, 2584 (1972); Allcock, H. R.; et al., *Macromolecules* 16, 715 (1983); Allcock, H. R.; et al., *Macromolecules* 19,1508 (1986); Allcock, H. R.; et al., *Biomaterials* 19, 500 (1988); Allcock, H. R.; et al., *Macromolecules* 21, 1980 (1988); Allcock, H. R.; et al., *Inorg. Chem.* 21(2), 515–521 (1982); Allcock, H. R.; et al., *Macromolecules* 22:75–79 (1989); U.S. Pat. Nos. 4,440,921, 4,495,174, 4,880,622 to Allcock, H. R.; et al.,; U.S. Pat. No. 4,946,938 to Magill, et al., U.S. Pat. No. 5,149,543 to Cohen et al., and the publication of Grolleman, et al., *J.Controlled Release* 3,143 (1986), the teachings of which, and polymers disclosed therein, are incorporated by reference herein.

Selection of an Antigen

The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

In one embodiment, the polymer is used to deliver nucleic acid which encodes antigen to a mucosal surface where the nucleic acid is expressed.

Examples of preferred antigens include viral proteins such as influenza proteins, human immunodeficiency virus (HIV) proteins, and hepatitis B proteins, and bacterial proteins and lipopolysaccharides such as gram negative bacterial cell walls and *Neisseria gonorrhea* proteins.

Preparation of an Immunogenic Composition

Combining Antigen with polymer for simultaneous administration.

An immunogenic composition, or vaccine, is prepared by combining the polymer adjuvant with an antigen. Approximately 0.5–0.0001 parts of antigen is added to one part polymer, preferably by stirring a solution of polymer and antigen until a solution or suspension is obtained, preferably for 10 minutes or more at 25° C. The polymer is preferably combined with the antigen using a method dispersing the antigen uniformly throughout the adjuvant. Methods for liquifying the polymer include dissolving the polymer in an aqueous-based solvent, preferably having a pH range of between 7.1 and 7.7, and melting the polymer. The latter is useful only when the antigen is stable at the polymer melting temperature. The antigen is then mixed with the polymer. The polymer and the antigen, in solid form, for example, when the antigen is lyophilized, can also be physically mixed together, for example, by compression molding. The polymer can also be used to encapsulate the antigen, for example, using the method of U.S. Pat. No. 5,149,543 to Cohen, et al., the teachings of which are incorporated herein, or by spray drying a solution of polymer and antigen. Alternatively, microspheres containing the antigen and adjuvant can be prepared by simply mixing the components in an aqueous solution, and then coagulating the polymer together with the substance by mechanical forces to form a microparticle. The microparticle can be stabilized, if necessary or desired, using electrolytes, pH changes, organic solvents, heat or frost to form polymer matrices encapsulating biological material.

In a preferred embodiment, approximately one part of polymer is dissolved in 10 parts 3% $Na_2CO_3$ aqueous solution while stirring, then 10 to 90 parts phosphate buffer pH 7.4 is slowly added.

Polymer-Antigen Conjugates

The polymer can also be covalently conjugated with the antigen to create a water-soluble conjugate in accordance with methods well-known to those skilled in the art, usually by covalent linkage between an amino or carboxyl group on the antigen and one of the ionizable side groups on the polymer.

Cross-linked Polymer Adjuvant

In an alternative preferred embodiment, the polymer is cross-linked with a multivalent ion, preferably using an aqueous solution containing multivalent ions of the opposite charge to those of the charged side groups of the polyphosphazene, such as multivalent cations if the polymer has acidic side groups or multivalent anions if the polymer has basic side groups.

Preferably, the polymers are cross-linked by di and trivalent metal ions such as calcium, copper, aluminum, magnesium, strontium, barium, tin, zinc, and iron, organic cations such as poly(amino acid)s, or other polymers such as poly-(ethyleneimine), poly(vinylamine) and polysaccharides.

Additives to the polymer-adjuvant mixture.

It will be understood by those skilled in the art that the immunogenic vaccine composition can contain other physiologically acceptable ingredients such as water, saline or a mineral oil such as Drakeol™, Markol™, and squalene to form an emulsion Administration of Polymer-Antigen Vaccine The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Nonlimiting examples of routes of delivery to mucosal surfaces are intranasal (or generally, the nasal associated lymphoid tissue), respiratory, vaginal, and rectal.

The dosage is determined by the antigen loading and by standard techniques for determining dosage and schedules for administration for each antigen, based on titer of antibody elicited by the polymer-antigen administration, as demonstrated by the following examples.

Although in the preferred embodiment the polymer-antigen mixture is administered simultaneously, in an alternative embodiment, the polymer and antigen are administered separately to the same or nearby site. The polymer serves to attract cells of the immune system to the site, where they process the antigen.

The polyphosphazene adjuvants and methods of synthesis will be further understood by reference to the following non-limiting examples.

EXAMPLE 1

Synthesis of poly[(carboxylatophenoxy)(glycinato)phosphazene].

Poly[(carboxylatophenoxy)(glycinato)phosphazene]was prepared as follows. Poly(dichlorophosphazene) (5.0, 0.0425 moles) was dissolved in 300 ml tetrahydrofuran (THF). The sodium salt of propyl p-hydroxybenzoate (prepared by reacting propyl hydroxybenzoate (30.6 g, 0.17 moles) with 60% sodium hydride (6.12, 0.15 moles) in THF) was added dropwise to the dissolved polymer. After addition of the sodium salt, the reaction mixture was stirred at reflux for 2 days and monitored by $^{31}P$ NMR.

Ethyl glycinate hydrochloride (23.63 g, 0.17 moles) was suspended in 50 ml toluene containing triethylamine (23.69, 0.17 moles) and refluxed for 3.5 hours. The reaction mixture was cooled in an ice bath and triethylamine hydrochloride precipitated from the solution. The solution was filtered and added to the polymer mixture at 0° C. The reaction mixture was allowed to warm to room temperature and stirred for 2 days. The polymer was purified by repeated precipitations into 100% ethanol.

The resulting polymer (0.5 g, 1.33 mmol) was dissolved in dry THF (20 ml). The solution was added slowly to a mixture of potassium tert-butoxide and water in dry THF. For the first 5 minutes, the mixture was cooled to 0° C.; it was then stirred at room temperature for 40 hours. A large excess of ice water (300 ml) was added, and the solution was concentrated by evaporation. The polymer was isolated by acidification of the solution with hydrochloric acid to pH 5.5. The conditions of reactions and weight average molecular weights of obtained polymers measured by gel permeation chromatography in water is shown in Table 1 below.

TABLE 1

Synthesis of poly[(carboxylatophenoxy)(glycinato)phosphazene].

| No | Concentration of polymer % w/v mol/l | Concentration of potassium tert-butoxide | Concentration of water mol/l | Reaction time hours | MW kDa |
| --- | --- | --- | --- | --- | --- |
| 1 | 0.42 | 0.30 | 0.1 | 42 | 80 |
| 2 | 0.42 | 0.15 | 0.05 | 18 | 130 |
| 3 | 0.42 | 0.04 | 0.05 | 5 | 170 |

The structures of polymers were confirmed by $^1$H and $^{31}$P NMR (JEOL FX90Q NMR spectrometer) and elemental microanalysis.

EXAMPLE 2

Synthesis of Poly[di(carboxylatophenoxy)phosphazene].

Poly[di(carboxylatophenoxy)phosphazene] was prepared by chemical modification of poly(dichlorophosphazene) with the sodium salt of propyl p-hydroxybenzoate, followed by hydrolysis of ester groups to carboxylic acid as described in Allcock, H. R. & Kwon, S. (1989) *Macromolecules* 22, 75–79, the teachings of which are incorporated herein.

EXAMPLE 3

Synthesis of poly[(carboxylatophenoxy)(chloro)phosphazene].

Poly[(carboxylatophenoxy)(chloro)phosphazene] was prepared as follows. Poly[di(chloro)phosphazene] (5.0 g, 0.0425 moles) was dissolved in 300 mL tetrahydrofuran (THF). The sodium salt of propyl p-hydroxybenzoate, prepared by reacting propyl hydroxybenzoate (30.6 g, 0.17 moles) with 60 % sodium hydride (6.12 g, 015 moles) in THF, was added dropwise to the dissolved polymer. After addition of the sodium salt, the reaction mixture was stirred at reflux for 2 days and monitored by $^{31}$P NMR. The polymer was purified by repeated precipitations into water, ethanol and hexane.

Poly[(propylhydroxybenzoate)(chloro)phosphazene] (2.0 g) was dissolved in 200 mL dry THF. 20 g potassium tert-butoxide was dissolved in 200 mL THF. The basic solution was cooled to 0° C. Water (1 mL) was added to the butoxide/THF solution and stirred for 5 minutes. The polymer solution then was added dropwise to the aqueous base. The reaction mixture was warmed to room temperature and stirred for 40 hours. After 40 hours, the reaction mixture was poured over an ice-water mixture and the THF was allowed to evaporate. The aqueous solution was then dialyzed against water for 2 days. After dialysis was complete, the dialysate was acidified with HCl and the resultant white precipitate, poly[(carboxylatophenoxy)(chloro)phosphazene], was washed with water and filtered from the solution.

EXAMPLE 4

Degradation of Phosphazene Polyelectrolytes

Degradation of phosphazene polyelectrolytes was studied in vitro at 37° C., in an air gravity incubator (Imperial II Incubator, Lab-Line Instruments, Inc.), with gentle agitation on a rotating shaker (ORBIT Shaker, Lab-Line Instruments, Inc., Melrose Park, Ill.) in vials containing a solution of 50 mg of polymer in 5 ml of 13 mM HEPES buffered saline solution (pH 7.4). The molecular weight of polyphosphazenes was determined by a Perkin-Elmer Series 10 liquid chromatograph with refractive index and a refractive index detector by using an Ultragel 2000 column (Waters Chromatography Division, Millipore Corporation, Cidra, Puerto Rico). 13 mM Hepes buffered saline solution (pH 7.4) was used as an eluant. Chromatograms were processed by GPC 5 and CHROM 2 software (Perkin-Elmer) to calculate the weight-average and number-average molecular weights using polyacrylic acid as a standard. The decline in polymer molecular weight over time is shown in Table 2.

TABLE 2

Degradation of Poly[(carboxylatophenoxy)(glycinato)phosphazene].

| Time days | Weight average molecular weight kDa | Number average molecular weight kDa |
| --- | --- | --- |
| 0 | 132.0 | 70.0 |
| 15 | 40.6 | 13.8 |
| 60 | 6.3 | 1.5 |
| 180 | 6.0 | 0.9 |
| 240 | 0.9 | 0.5 |

EXAMPLE 5

Antibody Titers after Immunization with Tetanus Toxoid in Various Concentrations of a Polyphosphazene Adjuvant.

Antibody titers were determined in female BALB/c mice, age 7 to 8 weeks, that had been inoculated with tetanus toxoid admixed with a polyphosphazene adjuvant.

An immunogenic composition containing tetanus toxoid in polyphosphazene was prepared as follows. 100 mg of poly[di(carboxylatophenoxy)phosphazene] was dissolved in 1 ml $Na_2CO_3$ and 1 ml phosphate buffered saline (PBS), pH 7.2 was added. 1.4 ml tetanus toxoid (2.2 mg/ml or 1000 LF/ml, Connaught Laboratories, Inc., Swiftwater, Pa.) was added with 0.6 ml containing 0.025% Brij solution (10 μl of 10% Brij 58, Sigma Chemical Co., St. Louis, Mo.) to the polymer.

Groups of five mice were immunized subcutaneously with a single dose of 25 μg tetanus toxoid admixed with dilutions containing 0.5% polyphosphazene, 0.05% polyphosphazene, or 0.005% polyphosphazene in $dH_{2O}$. A separate group of mice was immunized with a single subcutaneous dose of 25 μg of tetanus toxoid in complete Freund's adjuvant (SIGMA, St. Louis, Mo.). Blood samples were taken from the retroorbital sinus of $CO_2$ anaesthetized mice and analyzed by an ELISA immunoassay for anti-tetanus toxoid IgG.

As shown in Table 3 below, 25 μg of tetanus toxoid in 0.5% polyphosphazene gave anti-tetanus specific serum IgG titers slightly higher than the same dose in complete Freund's adjuvant. 25 μg of tetanus toxoid in 0.05% polyphosphazene gave titers that were slightly lower than the same dose in complete Freund's adjuvant. In all cases, the titer of antibody against tetanus toxoid was significantly higher when administered in conjunction with polymer than when administered alone.

TABLE 3

Anti-tetanus titers in mice after administration of tetanus toxoid with a polyphosphazene adjuvant or Freund's adjuvant.

| Group Treatment | Anti-tetanus toxoid ELISA titer (log 2) | | |
|---|---|---|---|
| | Week 3 | Week 5 | Week 7 |
| 25 µg TT/0.5% PP | 65536 (16) | 262144 (18) | 524288 (19) |
| 25 µg TT/0.05% PP | 16384 (14) | 32768 (15) | 32768 (15) |
| 25 µg TT/0.005% PP | 4096 (12) | 8192 (13) | 32768 (15) |
| 25 µg TT in Freund's | 16384 (14) | 131072 (17) | 262144 (18) |
| 25 µg TT in H$_2$O | 1024 (10) | 2048 (11) | 2048 (11) |

The letters "TT" are an abbreviation for tetanus toxoid whereas "PP" is an abbreviation for polyphosphazene.

EXAMPLE 6

Antibody Titers after Immunization with Various Concentrations of Tetanus Toxoid or Influenza Admixed with a Polyphosphazene Adjuvant.

Antibody titers were determined in female BALB/c mice, age 7 to 8 weeks, that had been inoculated with either influenza or tetanus toxoid admixed with the polyphosphazene adjuvant described in Example 5.

Two immunogenic compositions, one containing tetanus toxoid in polyphosphazene and the other containing influenza in polyphosphazene, were prepared as follows. 100 mg of poly[di(carboxylatophenoxy) phosphazene] was dissolved in 1 ml Na$_2$CO$_3$ and 1 ml phosphate buffered saline (PBS), pH 7.6 was added. Subsequently, tetanus toxoid (2.2 mg/ml) (Connaught Laboratories, Swiftwater, Pa.) or influenza (Influenza Branch, Center for Disease Control, Atlanta, Ga.) was diluted 1:10 in water and the appropriate volume of each was admixed with either 0.1% or 0.05% polyphosphazene.

Groups of three mice were immunized subcutaneously with a single dose of each immunogenic composition. Blood samples were taken from the retroorbital sinus of CO$_2$ anaesthetized mice after 21 days after inoculation and analyzed by an ELISA immunoassay for anti-tetanus toxoid or anti-influenza IgG.

The following influenza immunoassay protocol was performed to determine the influenza titers: 96-well ELISA microtiter plates were coated with influenza cell lysates at 10 µg/ml in carbonate buffer, pH 9.6, 100 ml per well and incubated 2 hours at 37° C. The plate was washed with 0.05% Tween 20/PBS (Sigma, St. Louis, Mo.) and 100 µl 12.5% bovine serum albumin/phosphate buffered saline (BSA/PBS) was added to each well as a blocking step. The plate was then incubated 1 hour at 37° C. and washed with 0.05% Tween 20/PBS. 50 µl 1% BSA/PBS was added to all wells. Serum samples were diluted to 1:128 by adding 5 µl serum to 635 µl % BSA/PBS. 50 µl of the dilute serum sample was added to the first well in a row, a 1:256 dilution. Both positive and negative controls were tested. Two-fold serial dilutions of serum sample were made by removing 50 µl from the first well in a row and adding the 50 µl with mixing to the second well; then removing 50 µl from the second well and adding it to the third well with mixing, and so on down the row, discarding 50 µl from the final or 12th well. The plates were then incubated 1 hour at 37° C. and the plate washed with 0.05% Tween 20/PBS. To each well was added 100 µl of OPD solution (0.4 mg/ml solution of 0-phenylenediamine dihydrochloride (Sigma, St. Louis, Mo.) in 0.05 M phosphate-citrate buffer pH 5.0 (1 OPD tablet per 12.5 ml citrate buffer) containing 0.05% hydrogen peroxide (20.8 µl 30% H$_2$O$_2$ per 12.5 ml citrate buffer)). The color was allowed to develop for 30 minutes, then stopped by addition of 50 µl 2M H$_2$SO$_4$/ well. The absorbance was read at OD$_{490}$, and the endpoint titer determined by finding the dilution of each serum sample that had an OD$_{490}$ greater than or equal to two times the OD$_{490}$ of the negative control at the same dilution.

As shown below in Tables 4 and 5, 25 mg of tetanus toxoid (TT) and 5 µg of influenza (flu), in combination with 0.1% polyphosphazene (PP), yielded serum IgG titers that were the same or higher than the same dose of antigen administered in complete Freund's adjuvant.

TABLE 4

Antibody Titers After Administration of Tetanus Toxoid Admixed with a Polyphosphazene Adjuvant or Freund's adjuvant.

| Treatment | Anti-Tetanus Toxoid Titer (log2) |
|---|---|
| 25 µg TT/0.1% PP | 16384 (14) |
| 5 µg TT/0.1% PP | 4096 (12) |
| 1 µg TT/0.1% PP | 2048 (11) |
| 0.2 µg TT/0.1% PP | 512 (9) |
| 25 µg TT/0.05% PP | 8192 (13) |
| 5 µg TT/0.05% PP | 4096 (12) |
| 1 µg TT/0.05% PP | 2048 (11) |
| 0.2 µg TT/0.05% PP | 512 (9) |
| 25 µg TT in water | 2048 (11) |
| 25 µg TT in Freund's | 16384 (14) |

TABLE 5

Antibody Titers After Administration of Influenza Admixed with a Polyphosphazene Adjuvant or Freund's adjuvant.

| Treatment | Anti-Influenza Titer (log2) |
|---|---|
| 5 µg flu/0.1% PP | 2048 (11) |
| 1 µg flu/0.1% PP | 4096 (12) |
| 0.2 µg flu/0.1% PP | <256 (<8) |
| 0.04 µg flu/0.1% PP | <256 (<8) |
| 5 µg flu/0.05% PP | 4096 (12) |
| 1 µg flu/0.05% PP | 1024 (10) |
| 0.2 µg flu/0.05% PP | <256 (<8) |
| 0.04 µg flu/0.05% PP | <256 (<8) |
| 5 µg flu in water | 256 (8) |
| 5 µg flu in Freund's | 512 (9) |

EXAMPLE 7

Influenza Hemagglutination Inhibition Titers after Immunization with Influenza Admixed with a Polyphosphazene Adjuvant.

An influenza hemagglutination inhibition antibody assay was performed with heat-inactivated mouse serum that had been incubated for 30 minutes with 10% chicken red blood cells (Spafas, Storrs, Conn.) to remove nonspecific inhibitors. Two-fold dilutions of sera were added to a 96-well microtiter plate and 8 hemagglutination (HA) units of virus suspension in a equal volume were added to each well and incubated at room temperature for 30 minutes. A 0.5% suspension of chicken red blood cells was added to each well and incubated at room temperature for 45–60 minutes.

Hemagglutination inhibition (HI) titers are expressed in Table 6 below as the reciprocal of the highest dilution that completely inhibits hemagglutination of erythrocytes.

As shown in Table 6, hemagglutination titers of animals inoculated with flu in combination with 0.1% polyphosphazene were high, while titers for flu in combination with complete Freund's adjuvant were negative.

TABLE 6

Hemagglutination Inhibition Titers After Administration of Influenza Admixed with a Polyphosphazene Adjuvant or Freund's adjuvant.

| Treatment Inhibition Titers | Hemagglutination |
|---|---|
| 5 µg flu/0.1% PP | 160 |
| 1 µg flu/0.1% PP | 320 |
| 0.2 µg flu/0.1% PP | 40 |
| 0.04 µg flu/0.1% PP | negative |
| 5 µg flu/0.05% PP | 160 |
| 1 µg flu/0.05% PP | 160 |
| 0.2 µg flu/0.05% PP | negative |
| 0.04 µg flu/0.05% PP | negative |
| 5 µg flu in water | negative |
| 5 µg flu in Freund's | negative |

EXAMPLE 8

Antibody Titers after Immunization with Tetanus Toxoid or Influenza Admixed with Various Concentrations of Two Different Polyphosphazene Polymer Adjuvants.

100 mg of poly[di(carboxylatophenoxy) phosphazene] (Polymer 1) was dissolved in 1 ml $Na_2CO_3$ and 3 ml of PBS was added to the polymer solution. 100 mg of poly[(carboxylatophenoxy)(glycinato)phosphazene] (Polymer 2) was dissolved in the same solvents.

Antibody titers were determined in groups of female BALB/c mice, three mice per group, age 7 to 8 weeks, 21 days after inoculation with 5 µg influenza admixed with one of each of the polymers.

As shown below in Table 7, 5 µg of flu in 0.1% or 0.05% of polymer 1 or polymer 2 give serum IgG titers that are higher than the same dosage of antigen in complete Freund's adjuvant.

TABLE 7

Antibody Titers After Administration of Influenza Admixed with Poly[di(carboxylatophenoxy)phosphazene] (Polymer 1), Poly[(carboxylatophenoxy)-(glycinato)phosphazene] (Polymer 2) or Freund's adjuvant.

| Treatment | Anti-Influenza Titer (log2) |
|---|---|
| 5 µg flu in water | <256 (<8) |
| 5 µg flu in Freund's | 256 (8) |
| 5 µg flu/0.1% Polymer 2 | 1024 (10) |
| 5 µg flu/0.05% Polymer 2 | 512 (9) |
| 5 µg flu/0.01% Polymer 1 | 4096 (12) |
| 5 µg flu/0.05% Polymer 1 | 4096 (12) |

Modifications and variations of the present invention, polymer adjuvants and methods of synthesis and use in vaccine compositions, will be obvious to those skilled in the art from the foregoing detailed description. Such modifications and variations are intended to come within the scope of the appended claims.

We claim:

1. A composition comprising:
   a synthetic water-soluble phosphazene polyelectrolyte consisting of a poly[di(carboxylatophenoxy)phosphazene-co-di(amino acid)phosphazene-co-(carboxylatophenoxy)(amino acid)phosphazene].

2. The composition of claim 1 wherein the phosphazene polyelectrolyte is cross-linked with a multivalent cation.

3. The composition of claim 2 wherein the multivalent cation is selected from the group consisting of calcium, copper, aluminum, magnesium, strontium, barium, tin, zinc, iron, poly(amino acid), poly(ethyleneimine), poly(vinylamine) and polysaccharides.

4. The composition of claim 1 wherein the phosphazene polyelectrolyte is biodegradable.

5. Poly[di(carboxylatophenoxy)phosphazene-co-di(glycinato)phosphazene-co-(carboxylatophenoxy)(glycinato) phosphazene].

6. Poly[di(carboxylatophenoxy)phosphazene-co-di(chloro)phosphazene-co-(carboxylatophenoxy)(chloro)phosphazene].

* * * * *